(12) United States Patent
Miyake et al.

(10) Patent No.: US 7,003,075 B2
(45) Date of Patent: Feb. 21, 2006

(54) OPTICAL MEASURING DEVICE

(75) Inventors: Akira Miyake, Utsunomiya (JP);
Fumitaro Masaki, Utsunomiya (JP)

(73) Assignee: Canon Kabushiki Kaisha, Tokyo (JP)

( * ) Notice: Subject to any disclaimer, the term of this patent is extended or adjusted under 35 U.S.C. 154(b) by 134 days.

(21) Appl. No.: 10/618,112

(22) Filed: Jul. 11, 2003

(65) Prior Publication Data
US 2004/0075830 A1    Apr. 22, 2004

(30) Foreign Application Priority Data
Jul. 12, 2002    (JP)    ............... 2002-204233

(51) Int. Cl.
*G01T 1/36*    (2006.01)
*G01N 23/20*    (2006.01)
(52) U.S. Cl. .......................................... 378/82; 378/70
(58) Field of Classification Search .................. 378/70, 378/82, 84, 85; 356/328, 334
See application file for complete search history.

(56) References Cited

U.S. PATENT DOCUMENTS

| | | | | |
|---|---|---|---|---|
| 5,160,848 A | * | 11/1992 | Saitoh et al. ............... | 250/548 |
| 5,377,009 A | * | 12/1994 | Kitaoka et al. ............. | 356/401 |
| 5,578,833 A | * | 11/1996 | Ohmi et al. ............. | 250/461.1 |
| 5,995,582 A | * | 11/1999 | Terashima et al. ............ | 378/34 |
| 6,312,373 B1 | * | 11/2001 | Ichihara ....................... | 356/515 |
| 2002/0033954 A1 | * | 3/2002 | Niu et al. .................... | 356/601 |
| 2002/0075996 A1 | * | 6/2002 | Holler et al. ................. | 378/82 |

FOREIGN PATENT DOCUMENTS

| | | | | |
|---|---|---|---|---|
| JP | 63058127 A | * | 3/1988 |
| JP | 08145916 A | * | 6/1996 |
| JP | 11264762 A | * | 9/1999 |
| SU | 1562716 A | * | 5/1990 |

* cited by examiner

*Primary Examiner*—Edward J. Glick
*Assistant Examiner*—Chih-Cheng Glen Kao
(74) *Attorney, Agent, or Firm*—Morgan & Finnegan, L.L.P.

(57) ABSTRACT

The present invention provides a measuring device by which, even if a radiation intensity from a light source, a beam size or a beam intensity distribution of the light source changes, an optical characteristic of an optical element to be measured can be measured very precisely. In a measuring device according to the present invention, to this end, light from a light source is diffracted by a diffracting grating to thereby resolve the same into plural light beams, and by using different light beams, the object to be measured is measured and the intensity of incident light from the light source is measured. With this structure, even if the light from the light source changes, the intensity of the light from the light source is specified concurrently, and therefore, the optical characteristic of the object to be measured can be measured very accurately.

14 Claims, 6 Drawing Sheets

OPTICAL MEASURING DEVICE

FIELD OF THE INVENTION AND RELATED ART

This invention relates generally to a measuring device and, more particularly, to a measuring device suitable to measurement of an optical characteristic such as a reflectivity or transmissivity, for example, of an optical element to be used with X-rays, soft X-rays, or EUV light (extreme ultraviolet light), for example.

Recently, many proposals have bean made in regard to semiconductor device manufacturing apparatuses designed to be used with light of extremely short wavelength such as X rays, soft X-rays, or EUV light, for example. In order to meet this, many proposals have been made in respect to measuring devices for measuring optical characteristics of optical elements to be used in such manufacturing apparatuses.

As an example of measuring device for evaluating the property (physical or chemical property) of a sample by irradiating the sample with soft X rays, there is a measuring device for measuring the reflectivity of a mirror or transmissivity of a filter. More specifically, in such measuring device, monochromatic light, that is, light of single wavelength, is projected upon a sample, and the intensity of light reflected by or transmitted through the sample is measured. Other examples are measuring device such as photoelectron spectrometric device, fluorescence X-ray analyzer, and etc. which are measuring devices for detecting interaction between the light and the sample, and they are used in many varieties of fields.

FIG. 12 is a schematic view or a reflectivity measuring device designed to be used with light of extremely short wavelength. The measuring device comprises a light source 1, a spectroscope MC, a condensing optical system 4, an incident light intensity monitor MO, and a sample chamber TR, for example. The light source 1 may comprise synchrotron radiation light or laser plasma light source, for example. The light source 1 does not emit light of single wavelength but it emits continuous spectrum light.

The spectroscope MC comprises a pre-mirror 2, an entrance slit S1, a diffraction grating 3, and an exit slit S2, for example. It has a monochrome function for extracting light of single wavelength, out of the continuous-spectrum light emitted from the light source 1. Also, the wavelength to be extracted can be set as desired in accordance with the measurement condition, and the wavelength can be scanned within a predetermined width, during the measurement process.

The condensing optical system 4 comprises a concave mirror (post-mirror), for example, and it has a function for concentrically projecting the monochromatic light to a small region on the sample Sa.

The intensity of light emitted from synchrotron radiation or laser plasma light source changes with time. More specifically, in the case of synchrotron light source, the amount of accumulated electrons decreases with time, and thus the intensity of light to be emitted decreases with time. In the case of laser plasma light source, the intensity of light to be emitted changes in response to a change in temperature, density or surface state of a target. Further, even a small change in the intensity of laser for exciting the laser plasma causes a large change in the intensity of light to be emitted.

The spectroscope MC comprises optical components such as diffraction grating 3, reflection mirror 2 and slits S1 and S2. If the position or attitude of these optical elements changes, the emission position or intensity of the light to be emitted therefrom changes. Such change in position or attitude of the optical elements may be caused by vibration of the floor where the apparatus is mounted or by a change in environment temperature.

Due to these factors, the intensity of light projected upon the sample Sa is not constant but it is changeable. In order to measure the interaction between the light and the sample accurately, it is a requisition to monitor the intensity of light projected upon tho sample. Here, the device to this end is referred to as "beam intensity monitor" or "incident light intensity monitor". The beam intensity monitor MO has a function for dividing a beam into plural beams, and it includes means for detecting the beam intensity while using one of the divided beams as a reference beam.

In the wavelength region of x-rays or EUV light, as regards the beam intensity monitor, there is a difficulty in relation to using a beam splitter such as a half mirror or a prism, for example, used in a visible light region as an element having a function for dividing a beam into plural beams. For this reason, conventional beam intensity monitors have included a sensor with a hole or a mesh-type detector. This is a detector such as a micro-channel plate or photodiode of a shape having a hole, and a light beam of a size larger than the hole is projected to the hole position. The projected beam is divided into a beam passing through the hole and a beam absorbed by a portion surrounding the hole. The beam passed through the hole irradiates the sample, while the absorbed beam is detected by the detector with respect to the intensity. Here, this detector is referred to as a first detector 7.

The sample chamber TR accommodates a stage for setting the sample Sa at desired position and angle with respect to the incident beam, and a second detector 8 for measuring the intensity of light passed through the sample or reflected by the surface of the sample. Also, the sample chamber is provided with a function for evacuating the inside thereof into a vacuum, to avoid absorption of light.

The reflectivity measurement for a sample Sa is carried out in accordance with the following procedure.

Without a sample Sa introduced, the light intensity is measured by use of the second detector 8. The value obtained here is denoted as S120. Simultaneously, the light intensity is detected by use of the first detector 7. The value obtained is denoted as S110.

Subsequently, with a sample Sa introduced, the intensity of light reflected by the sample is detected by use of the second detector 8. The valued obtained is denoted as S121. Simultaneously, the light intensity is detected by use of the first detector 7 of the incidence light intensity monitor MO. The value obtained is denoted as S111. Here, the reflectivity R of the sample is calculated by:

$$R=(S121/S120)\times(S110/S111)$$

The second term "S110/S111" is for correction of a change in light intensity of the light source. If there is no change in light intensity, the reflectivity can be calculated as:

$$R=S121/S120$$

As described above, in the beam intensity monitor of conventional measuring devices, among the light projected, the light having passed through a hole is projected upon the sample while the light intensity of the light blocked by a portion surrounding the hole is measured.

However, there is a possibility that the position, the size or the intensity distribution of a beam emitted from a spectroscope changes due to a change in position of the light source or in size of the light emitting portion thereof, a change in emission angle, or a change in position or angle of an optical element in the spectroscope such as diffraction grating, mirror or slit.

Therefore, in the case of the beam intensity monitor of the conventional measuring device shown in FIG. 12, if the position or size of the beam relative to the hole of the first detector 7 changes or the light intensity distribution within the beam changes, it results in a change in the measured value.

For example, if a uniform beam of a diameter 1 mm is detected by the first detector 7 having a hole diameter 0.8 mm, 36% of the incident beam is detected by the first detector while remaining 64% is projected upon the sample Sa. Here, if the beam diameter changes to 0.9 mm with the beam intensity unchanged, about 21% of the incident beam is detected by the first detector 7 and remaining approximate 79% is projected upon the sample. Although the intensity of light irradiating the sample Sa increases 1.23 times, the beam intensity detected by the first detector 7 reduces 0.58 times. Namely, if the beam size changes, it causes an error in the measurement.

Further, where the intensity distribution of the beam is not uniform, a change in positional relationship between the beam and the hole of the first detector or a change in the intensity distribution causes a measurement error.

SUMMARY OF THE INVENTION

It is accordingly an object of the present invention to provide a measuring device by which at least one of the inconveniences described above can be solved and by which the optical characteristic of an optical element (subject to be measured) can be measured very precisely regardless of a change in the radiation intensity, beam size or beam intensity distribution, for example, of a light source.

In accordance with an aspect of the present invention, to achieve above-described object, a measuring device includes a beam intensity monitor in which an incident light flux from a light source is diffracted by a diffraction grating and is divided thereby into plural light fluxes. A predetermined light flux of the plural light fluxes is directed through the subject of measurement to a second detecting device, while a light flux different from the predetermined light flux is directed to a reference light detecting photodetector, whereby the intensity of the incidence light from the light source is measured. With this arrangement, even if the light flux from the light source changes, since the intensity of the light flux from the light source can be specified simultaneously, the optical characteristic of the subject of measurement can be measured exactly.

These and other objects, features and advantages of the present invention will become more apparent upon a consideration of the following description of the preferred embodiments of the present invention taken in conjunction with the accompanying drawings.

DESCRIPTION OF THE PREFERRED EMBODIMENTS

Preferred embodiments of the present invention will now be described with reference to the attached drawings.

[Embodiment 1]

Figure 1:
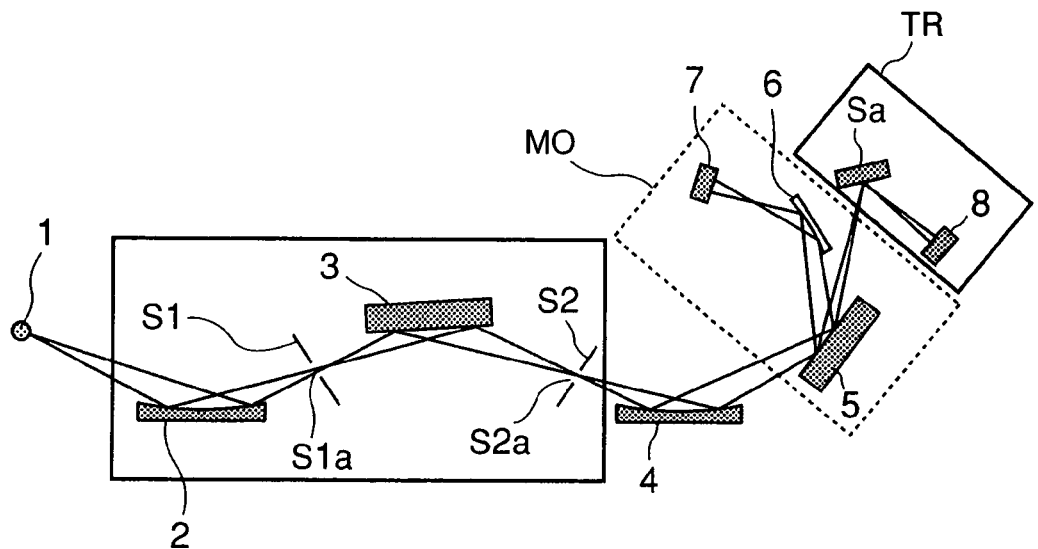
FIG. 1 is a schematic view of a main portion of a first embodiment of the present invention.

FIG. 1 is a schematic view of a main portion of a first embodiment of the present invention. FIG. 1 illustrates a measuring device for measuring the reflectivity of a sample Sa which is a multilayered film mirror in this example.

In FIG. 1, denoted at MC is a spectroscope, and denoted at MO is a beam intensity monitor (incident light intensity monitor). Denoted at TR is a sample chamber, and denoted at 1 is a light source which comprises a laser plasma light source for emitting X-rays and ultraviolet region.

Denoted at 2 is a pre-mirror for reflectively collecting light from the light source 1. It serves to direct the light toward an opening S1a of an entrance slit S1.

Denoted at 3 is a diffraction grating which functions to direct light of a predetermined wavelength, out of the light from the opening S1a of the entrance slit S1, toward and opening S2a of an exit slit S2.

Denoted at 4 is a post-mirror (curved surface reflection mirror) for directing light from the opening S2a of the exit slit S2, toward a diffraction grating 5.

The diffraction grating 5 diffracts light from the post-mirror 4. Among the diffracted light, zero-th order light is directed, as signal light, toward a sample Sa placed on a sample stage for reflectivity measurement, while diffraction light of orders other than the zero-th order is directed toward a condensing mirror 6 as reference light.

Reflection light from the sample Sa is received by a second detector 8, and light from the condensing mirror 6 is received by a monitoring (reference light detecting) first detector 7. The components 5, 6 and 7 are constituent elements of the incident light intensity monitor MO.

Before explaining the measuring device of the first embodiment shown in FIG. 1, the optical function for dividing the incident light into reference light and signal light by use of the diffraction grating 5 while consistently assuring a constant intensity ratio between them, and then for directing the light to the photodetector, will be described.

Figure 7:
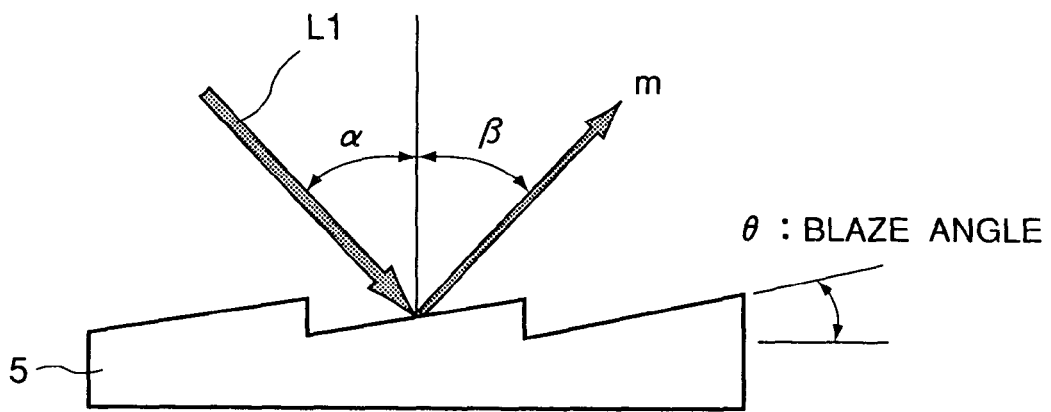
FIG. 7 is an illustration for explaining the relationship between a diffraction grating and light rays.

FIG. 7 is a schematic view of a reflection type plane diffraction grating. Where the groove interval of the diffraction grating 5 is d, the wavelength of the light L1 is λ, the incidence angle is α, and the diffraction angle is β, the relation of equation (1) below applies.

$$d \times (\sin \beta - \sin \alpha) = m \times \lambda \quad (1)$$

where m is the diffraction order and it takes an integral value.

If m=0, it means the case of zero-th order light and, in that occasion, $\alpha=\beta$. Namely, the incidence angle is equal to the diffraction angle, and it is equivalent to mirror reflection with respect to the surface of the diffraction grating 5. This situation is independent from the wavelength, as clearly seen from the equation. This is called zero-th order diffraction.

In this embodiment, diffraction light of an order m-0 is projected upon the sample. Diffraction light of any other order may be used to perform the sample measurement. On the other hand, where diffraction light of an order other than zero-th order of the diffraction grating 5 is projected upon the sample, there is a possibility that the projected position on the sample changes due to the wavelength of the diffraction light and, if the property of the sample is not uniform along its surface, an error may result from the difference. Further, for reflectivity measurement, the incidence angle may change. If the sample is small, it is possible that the sample is not irradiated with light. For these reasons, as regards the light to be projected upon the sample, for high-precision measurement it is desirable to use zero-th order light which does not cause a change in angle in dependence upon the wavelength.

In the beam intensity monitor MO of this embodiment, diffraction light of an order other than the zero-th order from the diffraction grating 5 is detected by a photodetector, and the beam intensity is measured. For example, if the order is 1, that is m=1, the diffraction condition can be expressed by equation (2) below.

$$d \times (\sin \beta - \sin \alpha) = \lambda \quad (2)$$

From this equation, equation (3) can be derived.

$$\sin \beta = \sin \alpha + \lambda/d \quad (3)$$

Figure 8:
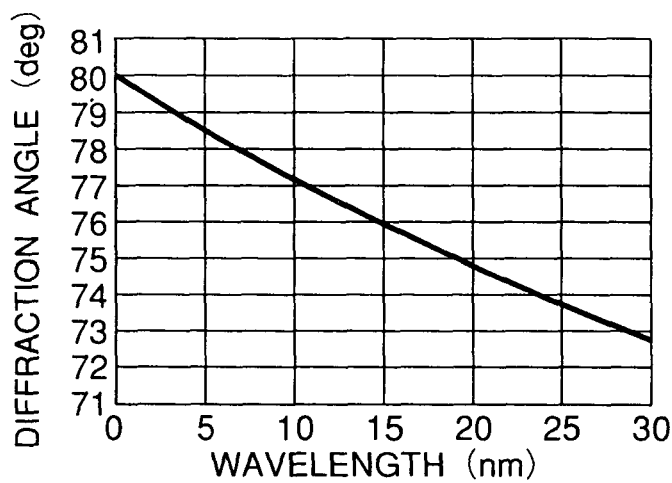
FIG. 8 is an illustration for explaining the relationship between the wavelength and the diffraction angle.
Figure 9:
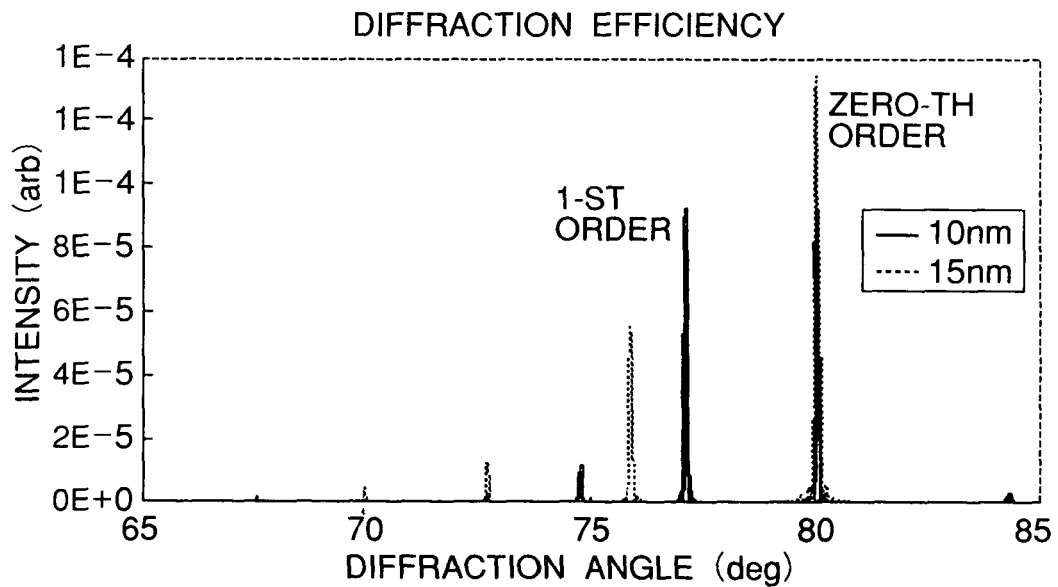
FIG. 9 is an illustration for explaining the diffraction efficiency of a blazed type diffraction grating.

It is seen from equation (3) that the diffraction angle $\beta$ of the first-order diffraction light is different, with the wavelength $\lambda$. FIG. 8 shows this relation. The calculation was carried out assuming that the groove interval d of the diffraction grating is 1 $\mu$m and the incidence angle $\alpha$ is 80 deg. FIG. 9 illustrates the result of calculation of the diffraction efficiency of a blaze type diffraction grating. Also in this example, it was assumed that the groove interval d of the diffraction grating was 1 $\mu$m and the incidence angle $\alpha$ was 80 deg. As regards the wavelength, the calculation was carried out for two conditions of 10 nm and 15 nm. It is seen that, although the zero-th order light is diffracted at the same angle even if the wavelength is different, the first order light is diffracted at different angles in dependence upon the wavelength.

Since the diffraction angle $\beta$ of the first-order diffraction light is different in dependence upon the wavelength $\lambda$, if for example the first order diffraction light is directly projected upon the first detector 7 which is provided at a position spaced away from the diffraction grating, the incidence position on the first detector 7 is different in dependence upon the wavelength. Where the incidence position on the detector is changeable when the wavelength to be used for the measurement is changed, there arises a possibility that the beam to be detected is not received by the light receiving surface of the detector, thus causing a failure of correct detection. Further, in order to avoid it, a detector having a large light receiving surface is required, and this leads to a problem of increase in size and cost of the measuring device.

In the beam intensity monitor MO of this embodiment, in consideration of the above-described inconveniences, first-order diffraction light is reflected by a concave surface mirror 5 thereby to assure that, even if the wavelength of light to be measured changes, the light is incident at a substantially constant position upon the light receiving surface of the first detector 7.

More specifically, it uses a condensing element which comprises a concave surface mirror 6 arranged so that its first focal point (object point) coincides with the incidence position of the diffraction grating 5 and its second focal point (image point) coincides with the center of the light receiving surface of the first detector 7. With this structure, even if the wavelength of light to be measured changes, light is incident substantially at a constant position upon the light receiving surface of the first detector 7.

The beam to be detected by the first detector 7 is not limited to first-order diffraction light. It may be diffraction light of a desired order, as long as it is different from zero-th order. Also in that occasion, since the diffraction angle of diffraction light of an order other than zero-th order changes with the wavelength, the diffraction light is reflected by use of the concave surface mirror 6, thereby to assure that the light is incident substantially at a constant position upon the light receiving surface of the first detector 7 regardless of a change in wavelength of light to be measured.

As regards reflection type diffraction gratings, diffraction gratings known in the art, such as blaze type or laminar type, for example, may be used. The shape of it may be selected so as to assure that the light intensity to be detected by the first detector 7 and the light intensity to be projected upon the sample are at a predetermined ratio.

Figure 10:
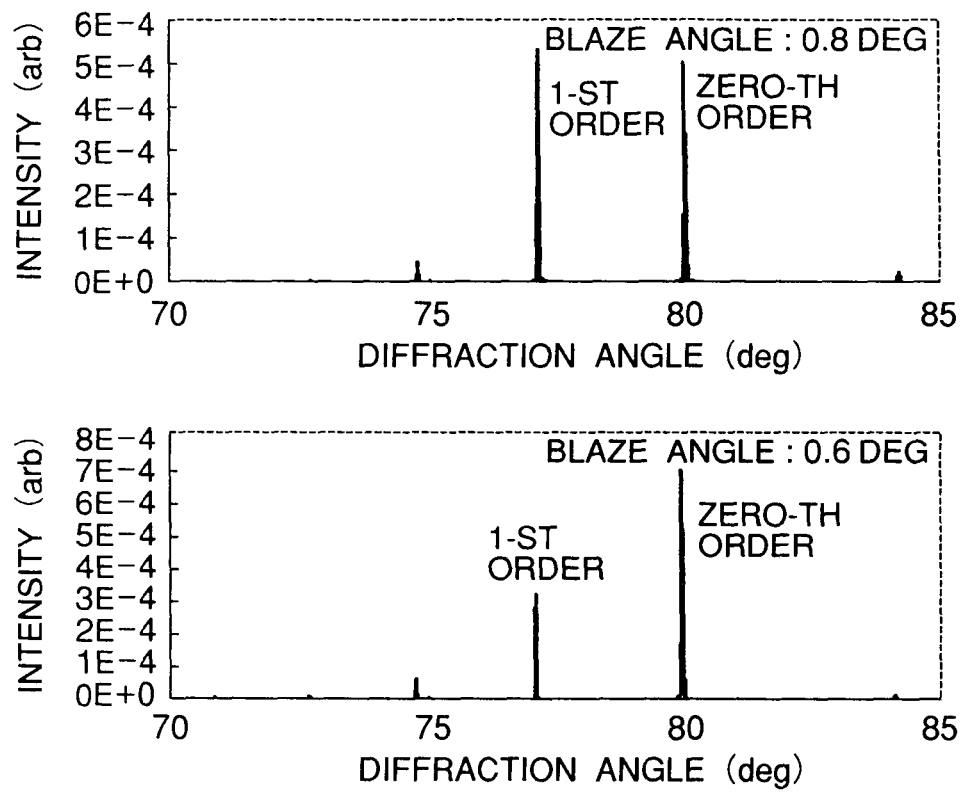
FIG. 10 is an illustration for explaining the diffraction efficiency of a blazed type diffraction grating.

FIG. 10 shows the result of calculation of the diffraction efficiency of a blaze type diffraction grating, with respect to different blaze angles. The calculation was carried out, assuming that the groove interval of the diffraction grating is 1 $\mu$m, incidence angle $\alpha$ is 80 deg., and the wavelength is 10 nm.

In this embodiment, by means of the diffraction grating 5, the light is divided on the basis of the optical property that zero-th order light and n-th order light consistently have a constant light intensity ratio even if the light intensity of incident light changes.

In the beam intensity monitor MO, it is desirable to distribute the light at an intensity ratio that enables best measurement precision. For example, where the reflectivity of a sample having a reflectivity of approximately 50% is going to be measured, the intensity of light to be projected upon the sample may be set to about twice the intensity of the light to be projected upon the first detector 7, and this may attain highest measurement precision.

Figure 11:
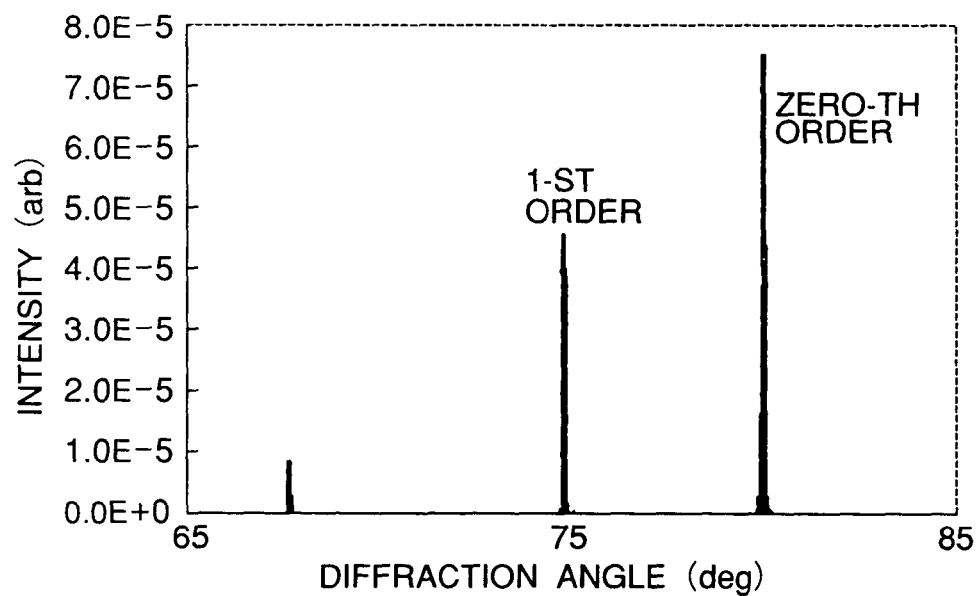
FIG. 11 is an illustration for explaining the diffraction efficiency of a laminar type diffraction grating.
Figure 12:
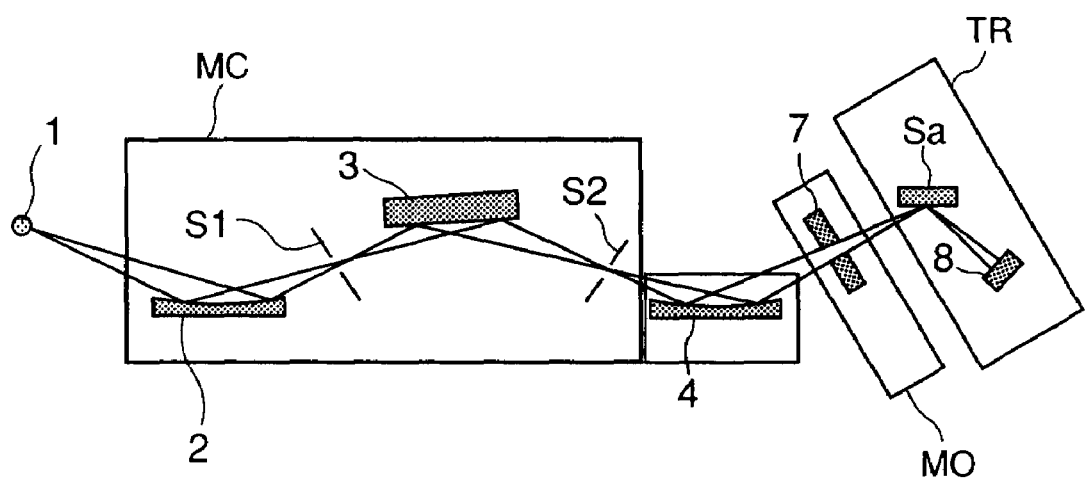
FIG. 12 is a schematic view of a conventional reflectivity measuring device.

The diffraction grating 5 is not limited to blaze type, but any type may be used. FIG. 11 shows the result of calculation of the diffraction efficiency of a laminar type diffraction grating. The calculation was carried out, assuming that the groove interval d of the diffraction grating is 1 $\mu$m, the incidence angle $\alpha$ is 80 deg., the wavelength is 10 nm, the groove depth is 90 nm, and the duty ratio is 0.5. In laminar type diffraction gratings, similarly, by choosing optimum groove depth and duty ratio (the ration between the groove pitch and the width of a portion other than the groove), since the diffraction efficiencies of respective orders are different, best setting may be done to assure highest measurement precision.

The functions of components shown in FIG. 1 will now be explained.

Generally, the reflectivity of a multilayered film mirror Sa depends on the incidence angle of light projected upon the mirror Sa. In consideration of it, in this embodiment, since that plasma light source 1 emits divergent light having continuous wavelength, by using an optical system, light being monochromatic is directed onto the sample Sa yet at the same incidence angle. The pre-mirror 2 takes EUV light from the light source 1, and an image of the light source 1 is imaged upon an opening of the slit S1. The slit S1 is provided here and, by adjusting the size of its opening, the size of the light source to be taken is restricted. Since the diffraction grating 3 diffracts incident light at an angle which is changeable with the wavelength, the slit S2 is provided at a downstream position to achieve spectral selection. More specifically, out of the light of continuous wavelength as emitted from the light source 1, light of a single wavelength is directed to the slit S2 by use of the spectroscope MC, thereby to extract measurement light. The diffraction grating 3 can be pivotally moved in accordance with the measurement condition, to set its wavelength as desired or to scan the wavelength within a predetermined width during the measurement process. The components such as pre-mirror 2, slit S1, diffraction grating 3 and slit S2, are constituent elements of a known constant-deviation monochrometer (spectroscope) MC.

The post-mirror 4 has a light collecting function, and it serves to form an image of the slit S2 upon the sample Sa. Thus, collected and monochromatic light is projected upon the sample Sa to be measured. The sample Sa and the photodetector 8 for detecting the intensity of reflection light are provided on a θ–2θ stage, and with this structure, the reflectivity of the sample Sa can be measured. Since the pre-mirror 2, diffraction grating 3 and post-mirror 4 are based on total reflection in the X-ray region, normally they are used in oblique incidence.

For measurement of the wavelength dependency of reflectivity of the sample Sa, the diffraction grating 3 of the spectroscope is rotated while the positions of the slits S1 and S2 are held fixed, and the wavelength scan is carried out and the wavelength of light to be emitted from the opening S2a of the slit S2 is changed.

Figure 2:
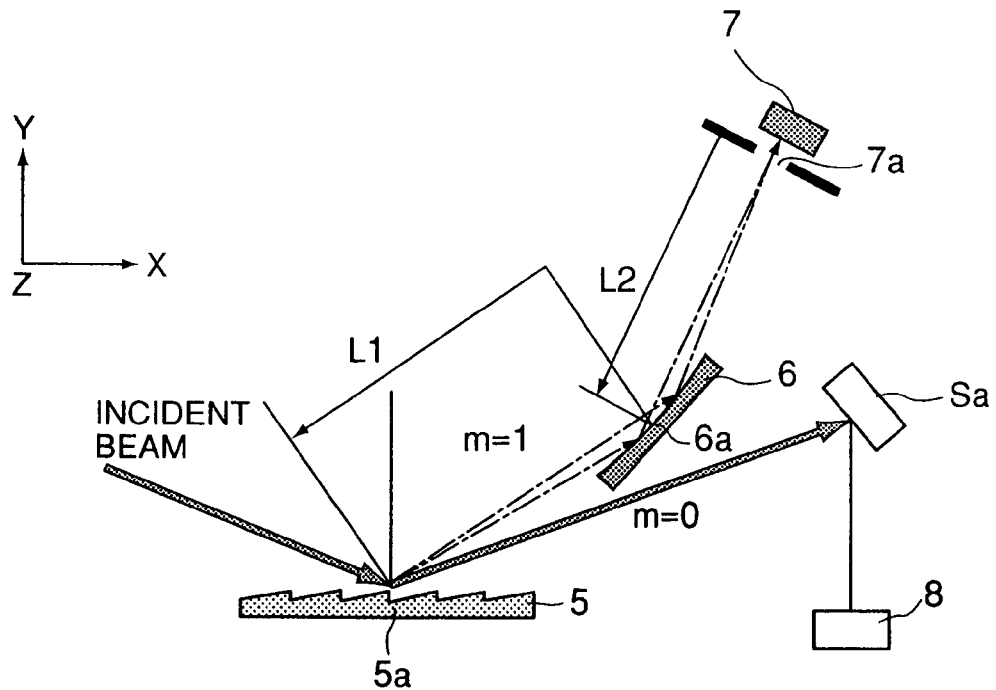
FIG. 2 is an enlarged and schematic view of a portion of FIG. 1.

In the laser plasma light source 1, the intensity of light to be emitted changes when the temperature, density or surface state of the target changes. Also, even a small change in the intensity of laser for exciting the laser plasma causes a large change in the intensity of light to be emitted. In this embodiment, in consideration of it, a measurement error due to a change in intensity of light emitted from the light source 1 is corrected. To this end, an incident light intensity monitor MO is provided along a light path between the post-mirror 4 and the sample Sa. FIG. 2 is an enlarged view of a portion of FIG. 1, after the diffraction grating 5.

The incidence light intensity monitor MO shown in FIG. 2 comprises a reflection type plane diffraction grating 5, a concave and cylindrical surface mirror 6, and a first detector 7. The plane diffraction grating 5 may be a diffraction grating of laminar or blaze type, having a groove interval of 0.5 µm.

Light reflected by a concave-surface toroidal mirror 4 is incident on the diffraction grating 5, and zero-th order diffraction light is projected upon the sample Sa. First-order diffraction light is reflected by the cylindrical surface mirror 6, and it impinges on the first detector 7. The first detector 7 comprises a photodiode.

Where the distance from the diffraction grating 5 (central point 5a) to the concave surface mirror 6 (central point 6a) is L1, and the distance from the concave surface mirror 6 (central point 6a) to the first detector 7 (opening 7a) is L2, the condition for assuring that light having different wavelengths and being diffracted by the diffraction grating 5 at different angles is incident on the same position upon the first detector 7, can be expressed by equation (4) below.

$$1/L1 + 1/L2 = 1/f \quad (4)$$

It follows from equation (4) that, where L1=L2=200 mm, for example, the focal length f of the concave surface mirror 6 is f=100 mm.

where the curvature radius of the concave mirror 6 is R1 and the incidence angle is θ when they are considered in respect to a plane (X-Y plane) defined by two straight lines, that is, an optical axis of the incident light and an optical axis of the reflection light of the concave surface mirror 6, then the focal length f of the concave mirror 6 can be expressed by equation (5) below.

$$f = (R1/2) \times \cos(\theta) \quad (5)$$

Thus, in the case of the above-described condition f=100 mm and θ=80 deg., from equation (5) it follows that R1=1152 mm. Namely, as regards the concave mirror 6, such a concave mirror as having curvature radius 1152 mm, when considered in terms of a plane (X-Y plane) defined by two straight lines of an optical axis (central axis) of incident light and an optical axis (central axis) of reflected light of the concave mirror 6, may be used.

By means of the post-mirror 4, the exit slit S2 and the diffraction grating 5 are placed in a conjugate relation with each other. Further, by means of the condensing mirror 6, the central portion of the diffraction grating 5 and the central portion of the first photodetector 7 are placed in an approximately conjugate relation with each other. With this structure, it is assured that, regardless that monochromatic light emits from the exit slit S2 at various angles, the reference light can be incident on the same position upon the photodetector 7.

As regards the curvature in respect to a direction perpendicular to the above-described plane, it may be determined to satisfy the condition that the beam reflected by the concave mirror 6 is just received by the light receiving surface of the first detector 7. Since, in respect to this direction, there is no difference in diffraction angle due to the wavelength, it is unnecessary to provide a large light condensing function.

Where the curvature radius if R2 and the incidence angle is θ when they are considered in regard to a plane (perpendicular plane), which is perpendicular to a plane (X-Y plane) defined by two straight lines of optical axes of incident light and reflection light of the concave mirror 6 and also which contains a normal to the concave mirror at the incidence point of the light, then the focal length f within the perpendicular plane can be expressed by equation (6) below.

$$f = (R2/2)/\cos(\theta) \quad (6)$$

In the case of oblique incidence, the focal length f becomes vary large, and there is no large light condensing function in that direction. In consideration of it, a spherical mirror with R2=R1 or a cylindrical mirror with R2=∞ may be used. As regards the concave mirror 6, a toroidal surface mirror or a revolutionally elliptical surface mirror may be used to assure that the light is collected exactly at the light receiving surface of the first detector 7. The curvature radii R1 and R2 in respective directions, in that occasion, may be optimized in accordance with ordinary ray tracing method, for example. Alternatively, a concave mirror having a revolutionally asymmetrical curved surface may be used.

Figure 3:
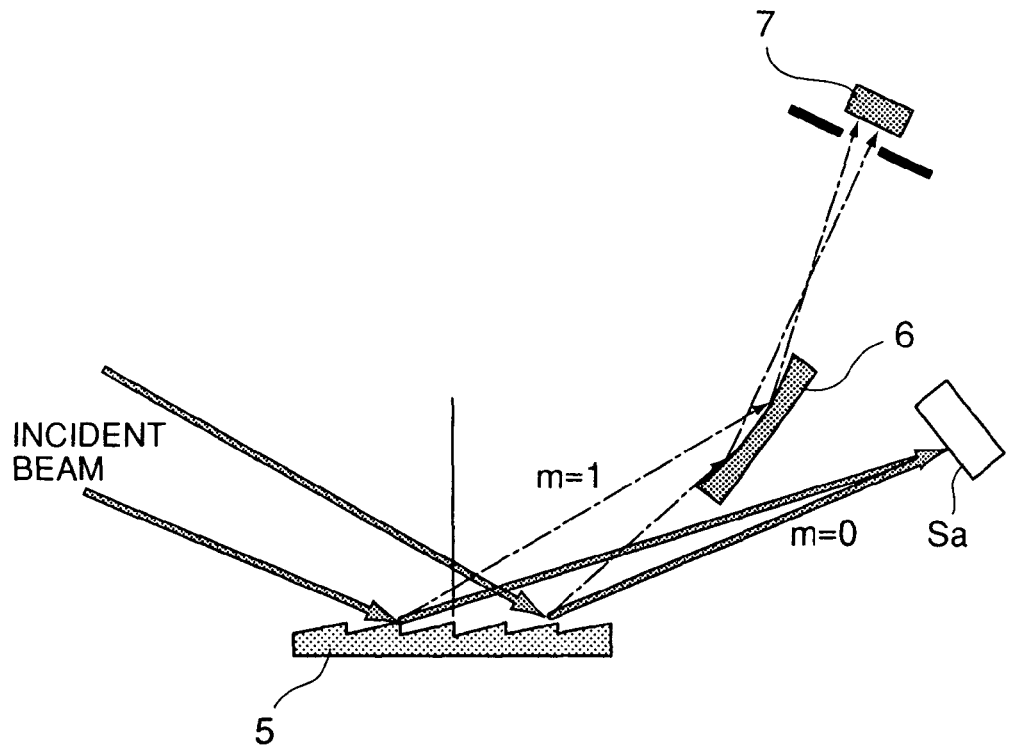
FIG. 3 is an enlarged and schematic view of a portion of FIG. 1.

In the foregoing description, angular dispersion of the beam incident on the incident light intensity monitor MO is not taken into account. In an optical system actually for measuring the reflectivity, the beam is subjected to a converging function by means of the post-mirror 4, such that light is concentrated to a small region upon the sample Sa. FIG. 3 is a schematic view, illustrating it. If the beam incident on the incident light intensity monitor MO is a convergent beam, in the case of an optical system arranged so as to satisfy the condition that the light having different wavelengths and being diffracted at different angles by the diffraction grating 5 is incident on the same position upon the detector 7, the light rays intersect with each other before they impinge upon the first detector 7. Therefore, the size of converged light upon the detector 7 becomes large. In such occasion, the focal length f of the concave surface condensing mirror 6 may be set to one longer than the focal length as determined by equation (7), and the size of converged light on the detector 7 can be made small thereby.

$$1/L1+1/L2=1/f \qquad (7)$$

However, in such case, there occurs a large change in light convergence position due to the wavelength scan. In consideration of it, a largest irradiation region upon the light receiving surface of the detector 7 may be considered while taking into account both the size of converged light and the change in convergence position with the wavelength scan, and the focal length of the concave condensing mirror may be determined to minimize it. Specifically, optimization can be done in accordance with ordinary ray tracing method, for example.

Figure 4:
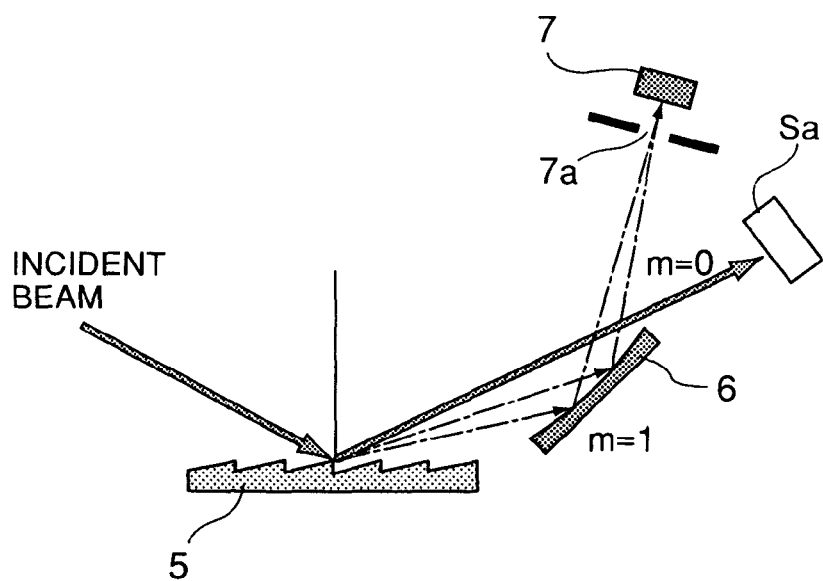
FIG. 4 is an enlarged and schematic view of a portion of FIG. 1, showing a different form.

In the above-described example, the first order diffraction light of the diffraction grating 5 of the incident light intensity monitor MO impinges on the first detector 7. However, the order is not limited to this. Light of any desired order other than zero-th order may be used. FIG. 4 is a schematic view of a case wherein negative first order (−1) diffraction light of the diffraction grating is incident on the first detector 7. In the example wherein first-order diffraction light of the diffraciton grating 5 impinges on the first detector 7, since the beam directed to the sample Sa passes behind the concave-surface condensing mirror 6, the thickness of the mirror 6 should be made small. On the other hand, in the case wherein negative first-order diffraction light of the diffraction grating 5 enters the first detector 7, the beam does not pass behind the condensing mirror 6. Therefore, there is no such limitation to the thickness of the mirror 6. Thus, the degree of freedom in regard to the method of manufacturing or holding the mirror is expanded.

However, in any case, the light to be projected upon the sample Sa must be zero-th order diffraction light of the diffraction grating 5, in order to avoid a change in incidence position due to a change in wavelength.

The sample chamber TR accommodates a stage for setting the sample Sa at desired position and angle with respect to the incident beam, and a second detector 8 for measuring the intensity of light passed through the sample Sa or reflected by the surface of the sample. Also, the sample chamber is provided with a function for evacuating the inside thereof into a vacuum, to avoid absorption of light.

The second detector 8 may comprise any ordinary detector, such as photodiode, charge coupled type image pickup device (CCD), micro-channel plate (MCP), electron mulitplier, or proportional counter, for example.

In this embodiment, the condensing mirror 6 may be omitted. In such occasion, if the position or angle of the beam emitted from the spectroscope MC changes, the incidence position of light upon the detection surface of the detector 7 also changes. In consideration of it, in this example, the detector 7 may desirably be a detector having a sensitivity being uniform as much as possible along the detector surface, to minimize the measurement error resulting therefrom. Also, where a detector such as CCD or MCP having a position resolving ability is used, the sensitivity of the detector may be measured beforehand as a function of the beam incidence position, such that, on the basis of the light intensity value measured in actual measurement and of the corresponding incidence position, sensitivity correction can be carried out in accordance with the function obtained beforehand. This enables further enhancement of the measurement precision.

The reflectivity measurement of the sample Sa is carried out in accordance with the following procedure. First, without a sample Sa introduced, the light intensity is measured by use of the second detector 8. The value obtained here is denoted as S120. Simultaneously, the light intensity is detected by use of the first detector 7. The value obtained is denoted as S110.

Subsequently, with a sample Sa introduced, the intensity of light reflected by the sample is detected by use of the second detector 8. The valued obtained is denoted as S121. Simultaneously, the light intensity is detected by use of the first detector 7 of the incidence light intensity monitor MO. The value obtained is denoted as S111.

The reflectivity R of the sample can be calculated in accordance with equation (8) below.

$$R=(S121/S120)\times(S110/S111) \qquad (8)$$

The second term "S110/S111" in equation (8) is for correction of a change in light intensity of the light source.

The above-described measurement is carried out repeatedly, while changing the angle of the diffraction grating 3 of the spectroscope MC and thus changing the wavelength of the light projected upon the sample Sa. With the sequential measurement operation, the wavelength dependency R(λ) of the reflectivity of the sample Sa can be measured very precisely.

As an alternative procedure, the following method may be adopted. First, without a sample Sa introduced, the wavelength scan is carried out, and the light intensity is measured by use of the second detector 8. The value obtained is denoted as S120(λ). Simultaneously, the light intensity is detected by use of the first detector 6 of the incidence light intensity monitor MO. The value obtained is denoted as S110(λ). Subsequently, with a sample Sa introduced, the wavelength scan is performed, and the intensity of light reflected by the sample Sa is detected by use of the second detector 8. The value obtained is denoted as S121(λ). Simultaneously, the light intensity is detected by use of the first detector 6 of the incident light intensity monitor MO. The value obtained is denoted as S111(λ).

The wavelength dependency R(λ) of the reflectivity of the sample Sa can be calculated by equation (9) below.

$$R=[S121(\lambda)/S120(\lambda)]\times[S110(\lambda)/S111(\lambda)] \qquad (9)$$

The second term "S110(λ)/S111(λ)" in equation (9) is for correction of a change in light intensity.

In this embodiment, even if the position of incidence light, the angle of incidence light, the shape of incidence light, or the size of incidence light, for example, changes with respect to the incident light intensity monitor, the incidence light can be divided by the diffraction grating 5 consistently at a constant proportion, such that one beam is projected upon the sample Sa while the other beam is reflected by a concave condensing mirror 6 and thereafter is projected approximately at the same position upon the light receiving surface of the detector 7, regardless of the wavelength. As a result, a change in the intensity of incident light, being projected upon the sample Sa, can be measured very accurately by means of the incident light intensity monitor MO. With this optical device, even if there occurs a change in intensity of light emitted from the light source 1 or a change in the optical elements 2 and 3 of the spectroscope MC, for example, such change can be corrected accurately. Thus, the characteristic of the sample Sa such as reflectivity or transmissivity, for example, can be measured very precisely.

Furthermore, since the sample Sa is irradiated with zero-th order diffraction light, being diffracted by the diffraction grating 5 of the incident light intensity monitor MO, there does not occur a change in incidence position or angle in dependence upon the wavelength. Therefore, the sample Sa can be measured under the same condition. Thus, there are advantageous effects that the measurement precision is high and that even a small sample Sa can be measured.

[Embodiment 2]

Figure 5:
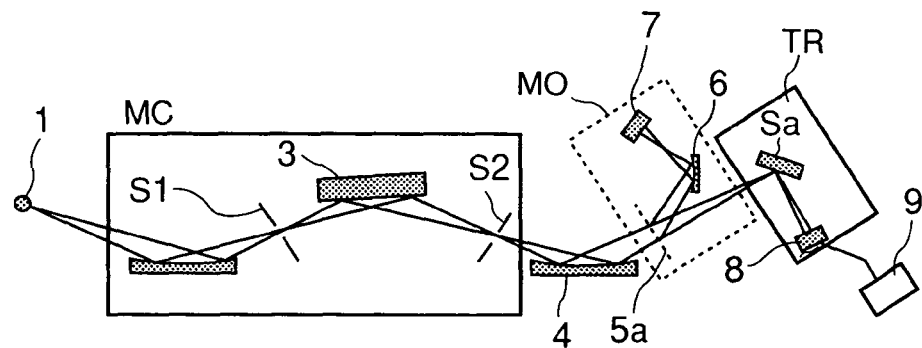
FIG. 5 is a schematic view of a main portion of a second embodiment of the present invention.

FIG. 5 is a schematic view of a main portion of a second embodiment of the present invention. FIG. 5 illustrates a device for measuring the characteristic of a sample Sa on the basis of photoelectron spectroscopy.

The photoelectron spectroscopy is a method of measuring energy spectrum of photoelectrons, emitted by external photoelectric effect in response to irradiating a sample Sa placed in a vacuum with high-energy monochromatic light. FIG. 5 illustrates a main portion of a measuring system of a photoelectron spectroscope MC. As major components, the device comprises a plasma light source 1, a spectroscope MC, a rotary stage, and a photoelectron energy analyzer TR.

Light from the light source 1 is made into monochromatic light by the spectroscope MC, under the structure similar to that of the reflectivity measuring device of the first embodiment, and the light is projected upon the sample Sa through an incident light intensity monitor MO. The light emitted from the sample Sa is detected by a photodetector 8 and, by analyzing the result by use of computing means 9, information peculiar to the sample Sa is obtained.

Figure 6:
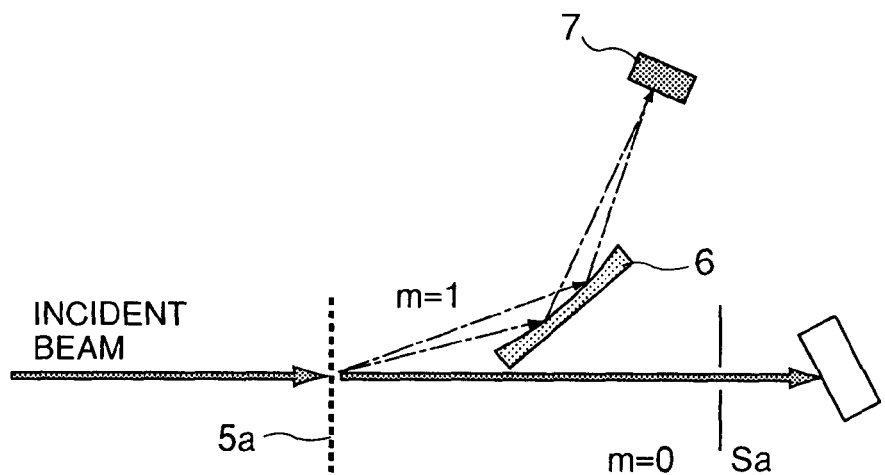
FIG. 6 is an enlarged and schematic view of a portion of FIG. 5.

FIG. 6 is a schematic view of the incident light intensity monitor MO of the optical device according to the second embodiment.

The light reflected by a post-mirror 4 impinges on a transmission type plane diffraction grating 5a, and zero-th order diffraction light passed through the grating straight is projected upon the sample Sa. First-order diffraction light (m−1) is reflected by a cylindrical surface mirror 6, and it enters a first detector 7. The first detector 7 comprises a photodiode.

In accordance with the second embodiment, even if the position of incidence light, the angle of incidence light, the shape of incidence light, or the size of incidence light, for example, changes with respect to the incident light intensity monitor, the incidence light can be divided by the transmission type diffraction grating 5a consistently at a constant proportion, such that one beam is projected upon the sample Sa while the other beam is reflected by a concave mirror 6 and thereafter is projected approximately at the same position upon the light receiving surface of the detector 7, regardless of the wavelength. As a result, a change in intensity of the beam (light), being projected upon the sample Sa, can be measured very accurately by means of the incident light intensity monitor MO. With this optical device, even if there occurs a change in intensity of light emitted from the light course 1 or a change in the optical element of the spectroscope MC (a change in position or optical characteristic thereof), for example, such change can be corrected accurately. Thus, the characteristic of the sample Sa such as photoelectron spectrum, for example, can be measured very precisely.

Furthermore, since the sample Sa is irradiated with zero th order diffraction light, being diffracted by the diffraction grating 5a of the incident light intensity monitor MO, there does not occur a change in incidence position or angle in dependence upon the wavelength. Therefore, the sample Sa can be measured under the same condition. Thus, there are advantageous effects that the measurement precision is high and that even a small sample Sa can be measured.

The beam intensity monitor according to the present invention can be applied to any device, provided that it is arranged to project X-rays (soft X-rays) to a sample and to perform the sample measurement on the basis of detecting the light (electromagnetic wave) reflected by or passed through the sample. For example, the invention is not limited to reflectivity measuring devices or photoelectron spectroscopes, but it can be applied to various devices where spectral measurement is to be done, such as reflection type XAFS, fluorescence XAFS, X-ray small-angle scattering, soft X-ray spectrometer, X-ray diffraction, XPS, AES, RHEED, REED, and the like.

While the invention has been described with reference to the structures disclosed herein, it is not confined to the details set forth and this application is intended to cover such modifications or changes as may come within the purposes of the improvements or the scope of the following claims.

What is claimed is:

1. A measuring device, comprising:
   a diffraction grating for diffracting light into a plurality of diffraction lights having different orders;
   a first detector for detecting an intensity of a diffraction light of a predetermined order, of said plurality of diffraction lights, which is not being reflected by an object to be measure; and
   a second detector for measuring an intensity of a diffraction light of an order different from the predetermined order, of said plurality of diffraction lights, which is being reflected by the object to be measured.

2. A measuring device according to claim 1, wherein the diffraction light to be detected by said second detector is zero-th order diffraction light diffracted by said diffraction grating.

3. A measuring device according to claim 1, further comprising a spectroscope for making the light to be projected upon said diffraction grating, into approximately monochromatic light.

4. A measuring device according to claim 3, wherein the approximately monochromatic light is one of EUV light, soft x-rays, and x-rays.

5. A measuring device according to claim 3, further comprising a curved-surface reflection mirror disposed between said spectroscope and said diffraction grating.

6. A measuring device according to claim 5, wherein, in a plane containing central axes of incident light and reflected light upon and from said curved-surface reflection mirror, an exit pupil of said spectroscope and said diffraction grating are approximately conjugate with each other with respect to said curved surface reflection mirror.

7. A measuring device according to claim 1, further comprising a condensing mirror provided between said diffraction grating and said first detector.

8. A measuring device according to claim 7, wherein said condensing mirror comprises one of a concave-surface toroidal mirror, a cylindrical mirror, a spherical mirror, and a revolutionally elliptical-surface mirror.

9. A measuring device according to claim 7, wherein, in a plane containing central axes of incident light and reflected light upon and from said condensing mirror, said diffraction grating and said first detector are approximately conjugate with each other with respect to the condensing mirror.

10. A measuring device according to claim 1, wherein said diffraction grating is a plane diffraction grating of laminar type or blaze type.

11. A device according to claim 1, wherein a change in a result of measurement of said second detecting means due to a change in an intensity of rays emitted from a light source and incident on said diffraction grating is compensated using a result of measurement of said first detector.

12. A device according to claim 1, further comprising a concave reflection mirror, disposed between said diffraction grating and said first detector for providing a conjugate relation between said diffraction grating and said first detector, wherein the incident light comprises a plurality of different wavelengths.

13. A measuring device according to claim 1 further comprising
a concave reflecting mirror, disposed between said diffraction grating and said first dectector, for providing a substantially conjugate relationship between said diffraction grating and said first detector.

14. A device according to claim 13, wherein zero-th order diffraction light emergent from said diffraction grating is directed to said second detector.

* * * * *